US011536955B2

United States Patent
Petit

(10) Patent No.: US 11,536,955 B2
(45) Date of Patent: Dec. 27, 2022

(54) FIBRE EXCITATION WITH PIEZO BENDER ACTUATORS

(71) Applicant: Blickfeld GmbH, Munich (DE)

(72) Inventor: Florian Petit, Munich (DE)

(73) Assignee: Blickfeld GmbH, Munich (DE)

( * ) Notice: Subject to any disclaimer, the term of this patent is extended or adjusted under 35 U.S.C. 154(b) by 863 days.

(21) Appl. No.: 16/336,594

(22) PCT Filed: Sep. 26, 2017

(86) PCT No.: PCT/DE2017/100818
§ 371 (c)(1),
(2) Date: Jun. 17, 2019

(87) PCT Pub. No.: WO2018/054429
PCT Pub. Date: Mar. 29, 2018

(65) Prior Publication Data
US 2019/0310465 A1 Oct. 10, 2019

(30) Foreign Application Priority Data

Sep. 26, 2016 (DE) ...................... 10 2016 011 647.1

(51) Int. Cl.
| | |
|---|---|
| G02B 26/10 | (2006.01) |
| H02N 2/04 | (2006.01) |
| H02N 2/06 | (2006.01) |
| H04B 10/2575 | (2013.01) |
| A61B 1/07 | (2006.01) |
| B06B 1/06 | (2006.01) |

(Continued)

(52) U.S. Cl.
CPC ............ *G02B 26/103* (2013.01); *A61B 1/07* (2013.01); *B06B 1/0603* (2013.01); *H02N 2/043* (2013.01); *H02N 2/062* (2013.01); *H04B 10/2575* (2013.01); *A61B 1/00165* (2013.01); *A61B 1/00172* (2013.01); *H01Q 1/3275* (2013.01)

(58) Field of Classification Search
None
See application file for complete search history.

(56) References Cited

U.S. PATENT DOCUMENTS 6,845,190 B1 * 1/2005 Smithwick ............ G02B 26/10
 385/11
2002/0057863 A1 5/2002 Nahum
(Continued)

FOREIGN PATENT DOCUMENTS

JP 2013081680 A * 5/2013
WO WO-2014147870 A1 * 9/2014 ......... A61B 1/00172

OTHER PUBLICATIONS

International Search Report dated Mar. 5, 2017 in connection with International Application No. PCT/DE2017/100818.
(Continued)

*Primary Examiner* — Chad H Smith
(74) *Attorney, Agent, or Firm* — Eschweiler & Potashnik, LLC

(57) ABSTRACT

A device (100) for the excitation of a fiber (150) comprises a first piezo bender actuator (110) and a second piezo bender actuator (120). The device (100) also comprises a connection part (130) which is arranged between the first piezo bender actuator (110) and the second piezo bender actuator (120). The device (100) also comprises a movable fiber (150) which is mounted to the connection part (130).

24 Claims, 11 Drawing Sheets

(51) Int. Cl.
*A61B 1/00* (2006.01)
*H01Q 1/32* (2006.01)

(56) References Cited

U.S. PATENT DOCUMENTS

| | | |
|---|---|---|
| 2010/0177368 A1* | 7/2010 | Kobayashi .......... A61B 1/0008 |
| | | 359/198.1 |
| 2013/0138337 A1 | 5/2013 | Pack |
| 2014/0354790 A1 | 12/2014 | Yuji |
| 2016/0231561 A1 | 8/2016 | Kasai |
| 2017/0010461 A1 | 1/2017 | Yasuaki |
| 2017/0371036 A1 | 12/2017 | Griffin |

OTHER PUBLICATIONS

Leach, Jeffrey, et al.; "Monostatic All-Fiber Scanning LADAR System", Applied Optics Research Article, vol. 54, No. 33; Nov. 20, 2015.
Rivera, David, et al.; "Compact and Flexible Raster Scanning Multiphoton Endoscope Capable if Imaging Unstained Tissue"; School Of Applied Engineering Physics, Cornell University; vol. 108, No. 43; Oct. 25, 2011.
"Piezoelectric Actuators"; PI Ceramic GmbH; www.piceramic.com.

* cited by examiner

FIBRE EXCITATION WITH PIEZO BENDER ACTUATORS

REFERENCE TO RELATED APPLICATIONS

This application is a National Phase entry application of International Patent Application No. PCT/DE2017/100818 filed Sep. 26, 2017, which claims priority to German Application 10 2016 011 647.1 filed Sep. 26, 2016, the contents of which are hereby incorporated by reference in their entirety.

TECHNICAL FIELD

The invention relates in general to the excitation of a fiber. The invention relates in particular to the excitation of a fiber with a first piezo bender actuator and with a second piezo bender actuator.

BACKGROUND

In various fields of the art, it can be desirable to excite a fiber, i.e., to bring about a motion of the fiber. For example, by means of the motion of the fiber, an endoscope can be implemented. See, for example, Rivera, David R., et al. "Compact and flexible raster scanning multiphoton endoscope capable of imaging unstained tissue." Proceedings of the National Academy of Sciences 108.43 (2011): 17598-17603. The motion of the fiber can also be used to scan pulsed laser light. See, for example, Leach, Jeffrey H., Stephen R. Chinn, and Lew Goldberg. "Monostatic all-fiber scanning LADAR system." Applied optics 54.33 (2015): 9752-9757.

Often tubular piezo actuators are used for the excitation of the fiber. Said tubular piezo actuators can extend, for example, along a longitudinal axis of the fiber. See, for example, Smithwick, Q, Y. J. et al. "Modeling and control of the resonant fiber scanner of a novel scanning scope." Engineering in Medicine and Biology, 2002. 24th Annual Conference and the Annual Fall Meeting of the Biomedical Engineering Society EMBS/BMES Conference, 2002. Proceedings of the Second Joint. Vol. 2. IEEE, 2002.

However, such techniques have certain disadvantages and limitations. For example, with a given geometry of the excitation, an amplitude of the motion can be relatively limited. This can limit the field of view for optical applications. Furthermore, the degrees of freedom of motion which can be excited by means of a corresponding geometry of the excitation can be limited.

BRIEF SUMMARY OF THE INVENTION

Therefore, there is a need for improved techniques for the excitation of a fiber. In particular, there is a need for such techniques which alleviate or eliminate at least some of the above-mentioned disadvantages and limitations.

This aim is achieved by the features of the independent claims. The features of the dependent claims define embodiments.

In an example, a device for the excitation of a fiber comprises a first piezo bender actuator and a second piezo bender actuator. The device also comprises a connection part. The connection part is arranged between the first piezo bender actuator and the second piezo bender actuator. The device also comprises a movable fiber which is mounted to the connection part.

In an additional example, a method comprises controlling a first piezo bender actuator with a first signal form and controlling a second piezo bender actuator with a second signal form. Thereby, it is achieved that a movable fiber on a connection part arranged between the first piezo bender actuator and the second piezo bender actuator is excited.

In an additional example, a system comprises an elongate first housing and an elongate second housing. The elongate second housing extends at least in a section along the first housing. The system also comprises a high-frequency antenna. The high-frequency antenna is arranged in the first housing. The system also comprises a device with a first piezo bender actuator and with a second piezo bender actuator, a connection part and a movable fiber according to various other examples described herein.

Such examples can be combined with one another in various additional examples.

DETAILED DESCRIPTION OF EMBODIMENTS

Figure 1:
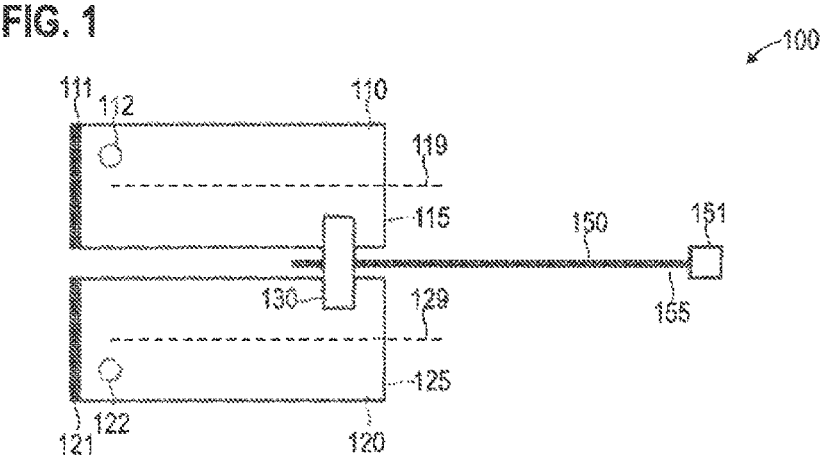
FIG. 1 diagrammatically illustrates a device for the excitation of a fiber, which comprises two piezo bender actuators according to different embodiments.

The above-described characteristics, features and advantages of this invention and the manner in which they are achieved are clarified and can be better understood in the context of the following description of the embodiment examples which are explained in further detail in reference to the drawings.

Below, the present invention is explained in further detail based on preferred embodiments in reference to the drawings. In the figures, identical reference numerals denote identical or similar elements. The figures are diagrammatic representations of different embodiments of the invention. Elements represented in the figures are not necessarily represented true to scale. Instead, the different elements represented in the figures are reproduced in such a manner that their function and general purpose are understandable to the person skilled in the art. Connections and couplings between functional units and elements represented in the figures can also be implemented as indirect connection or coupling. A connection or coupling can be implemented in a wired or wireless manner. Functional units can be implemented as hardware, software or as a combination of hardware and software.

Below, techniques for the excitation of a fiber-shaped element are described (for the sake of brevity, the fiber-shaped element is referred to simply as fiber below). The excitation of the fiber brings about a motion of the fiber. In the different examples described herein, different motions and degrees of freedom of motion of the fiber can be excited. Examples include a torsion mode in which the fiber undergoes a twisting along the longitudinal axis thereof. Additional examples comprise one or more transverse modes, in which the fiber is deflected perpendicularly to the longitudinal axis thereof. In some examples, it is possible to excite transverse modes of different orientation—for example, perpendicular with respect to one another—, i.e., orthogonal transverse modes. In some examples, it is possible that transverse modes of different order are excited, for example, of first order or of second order. The transverse modes of different order can have a different number of nodes and bulges.

Different types of fibers can be used. For example, optical fibers can be used, which are also referred to as glass fibers. However, this is not necessary. In fact, here the fibers do not have to be produced from glass. The fibers can be produced, for example, from plastic, glass, silicon or another material. For example, the fibers can be produced from quartz glass. For example, the fibers can have a modulus of resilience of 70 GPa or a modulus of resilience in the range of 40 GPa-80 GPa, preferably in the range 60-75 GPa. For example, the fibers can have a modulus of resilience in the range of 140 GPa-200 GPa. For example, the fibers can enable up to 4% material elongation. In some examples, the fibers have a core in which the fed-in laser light propagates and is enclosed by total reflection at the margins (optical waveguide). However, the fiber does not have to have a core. In various examples, so-called single mode optical fibers (single mode fibers) or multimode optical fibers (multimode fibers) can be used. The different fibers described herein can have a circular cross section, for example. For example, it would be possible for the different fibers described herein to have a diameter which is not less than 50 µm, optionally not <150 µm, further optionally not <500 µm, further optionally not <1 mm. However, the diameter can also be <1 mm, optionally <500 µm, further optionally less than 150 µm. For example, the different fibers described herein can be designed so that they can be bent or curved, i.e., so as to be flexible. For this purpose, the material of the fibers described herein can have a certain resilience. Therefore, the fibers can also be referred to as spring elements. The fibers can have, for example, a length in the range of 3 mm to 12 mm, optionally in the range of 4 mm to 8 mm.

The excited fiber can be used in a wide variety of fields of application. Examples include, for example, the distance measurement by means of pulsed laser light (also referred to as light detection and ranging, LIDAR; sometimes also LADAR). In such a case, it would be possible for the laser light to be led through an optical waveguide in the region of the core of the fiber and exit from the fiber at the movable end of the fiber. However, alternatively or additionally it would also be possible for the laser light to not to propagate through the fiber and to be deflected, for example, by a deflecting unit—such as a prism or a mirror—which is mounted at the movable end of the fiber. For example, a back side fastening of a mirror can be used: here, the fiber can extend away from a back side of the mirror, which is opposite the mirror surface. Thus, it can be possible to scan the pulsed laser light. An additional field of application would be endoscopy, for example. An additional field of application would be, for example, a projector which scans visible light of different colors such as red, green and blue, for example.

Below, various techniques for scanning light are described. The techniques described below can enable, for example, the one-dimensional or two-dimensional scanning of light. Scanning can denote repeated emission of light at different radiation angles or angular ranges. The repeated implementation of a certain angular range can determine a refresh rate of the scanning. The value of the angular ranges can define a scanning range or an imaging region. The scanning can denote the repeated scanning of different scanning points in the surroundings by means of the light. For each scanning point, measurement signals can be determined.

In some examples, a one-dimensional scanning range is implemented. For this purpose, it would be possible, for example, to excite a single degree of freedom of motion of the fiber in a targeted manner. However, in additional examples, a two-dimensional scanning range can be implemented. For this purpose, it can be possible, for example, to excite a first degree of freedom of motion of the fiber superposed with a second degree of motion of the fiber. This means that the fiber can carry out temporally and spatially superposed motions. For example, it would be possible to excite a transverse mode of the fiber which is superposed with a torsion mode of the fiber. For example, it would be possible to excite the transverse mode of first order and/or of second order of the fiber superposed with a torsion mode of the fiber.

In various examples, the fiber can be excited in a resonant manner, that is to say at or close to a resonance frequency. For example, the fiber can be excited in a semi-resonant manner, i.e., in the flank of a resonance curve.

In different examples, piezo bender actuators can be used for the excitation of the fiber. For example, a first and a second piezo bender actuator can be used. It would be possible for the first piezo bender actuator and/or the second piezo bender actuator to be designed in the form of a plate. In general, a thickness of the piezo bender actuators can be, for example, in the range of 200 µm-1 mm, optionally in the range of 300 µm-700 µm. For example, it would be possible for the first piezo bender actuator and/or the second piezo bender actuator to have a layer structure comprising an alternating arrangement of several piezoelectric materials. Said piezoelectric materials can have a piezoelectric effect of different strength. Thereby, a bending can be brought about, similar to a bimetallic strip in the case of temperature changes. For example, it is possible for the first piezo bender actuator and/or the second piezo bender actuator to be fastened at a fastening site: an end opposite the fastening site can then be moved due to a bending or curving of the first piezo bender actuator and/or of the second piezo bender actuator.

By using piezo bender actuators, a particularly efficient and strong excitation of the fiber can be achieved. In addition, it is possible to achieve a high integration of the device for the excitation of the fiber. This can mean that the necessary installation space can be dimensioned to be particularly small.

Figure 2:
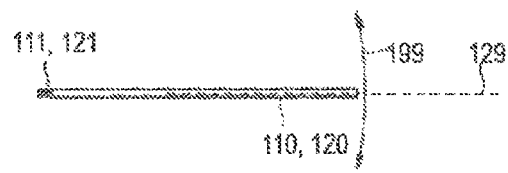
FIG. 2 diagrammatically illustrates a piezo bender actuator according to different embodiments.

FIG. 1 illustrates aspects with regard to a device 100. In particular, FIG. 1 illustrates aspects with regard to an arrangement of piezo actuators 110, 120 with respect to a fiber 150. In the example of FIG. 1, the piezo actuators 110, 120 are designed as piezo bender actuators. This means that the application of a voltage to electrical contacts 112, 122 of the piezo bender actuators 110, 120 brings about a curving or bending of the piezo bender actuators 110, 120 along the longitudinal axis 119, 129 thereof. For this purpose, the piezo bender actuators 110, 120 have a layer structure (not represented in FIG. 1 and oriented perpendicular to the plane of the drawing). In this way an end 115, 125 of the piezo bender actuators 110, 120 is deflected with respect to a fastening site 111, 121 perpendicular to the respective longitudinal axis 119, 129 (in the example of FIG. 1, the deflection is oriented perpendicular to the plane of the drawing). The deflection 199 of the piezo bender actuators 110, 120 due to the bending is not represented in FIG. 2. FIG. 2 is a side view of the piezo bender actuators 110, 120. FIG. 2 shows the piezo bender actuators 110, 120 in a resting position, for example, without driver signal or tension/curving.

For example, the fastening sites 111, 121 can establish a rigid connection between the piezo bender actuators 110, 120 and a housing of the device 100 (not represented in FIG. 1).

In the example of FIG. 1, the device 100 also comprises a connection part 130. The connection part 130 is arranged between the piezo bender actuators 110, 120 in a region adjoining the movable ends 115, 125. Thereby, a deflection 199 of the piezo bender actuators 110, 120 and also a motion of the connection part 130 are brought about.

The connection part 130 is also connected to the fiber 150, for example, by adhesive. The connection part 130 could also be designed to form a single piece with the fiber 150. Thereby, a motion of the piezo bender actuators 110, 120 is transferred via the connection part 130 to the fiber 150. The fiber 150 extends away from the connection part 130. Thereby, the fiber 150 can be excited. For example, a transverse mode and/or a torsion mode of the fiber 150 could be excited. The result of this is, in particular, that a movable end 155 of the fiber 150, which is arranged opposite the connection part 130, can be moved. For example, a curving or twisting of the fiber 150 in the region of the movable end 150 by a transverse mode or a torsion mode can be achieved.

The fiber can also be continued beyond the connection part 130 in a direction away from the movable end (shown only in sections in FIG. 1). Then, for example, light can be fed into the fiber and led to the movable end 155.

The device 100 enables a particularly efficient excitation of the fiber 150. For example, motions of the fiber 150 with a particularly large amplitude can be excited. In addition, it has been observed that, by means of the device 100, the torsion mode of the fiber 150 can be excited particularly efficiently.

At the movable end 155 of the fiber 150, an optical element 151 is also mounted. The optical element 151 can convert the motion of the fiber 155 into a deflection of light, for example, of laser light. Thereby, the light can be scanned. In some example, the light can extend along the longitudinal axis through the fiber 150, for example, in an optical waveguide close to the core of the fiber 150. However, in other examples, the light can also reach the optical element 151 by another path. For example, the optical element 151 can have a lens such as, for example, a GRIN lens (graded index lens). For example, it would be possible for the optical element 151 to have a deflecting unit, for example, a mirror or a prism.

In the example of FIG. 1, the longitudinal axis 119 of the piezo bender actuator 110 is parallel to the longitudinal axis 129 of the piezo bender actuator 120. This means that the longitudinal axes 119, 129 enclose an angle of approximately 0° with one another. In general, it is possible that the longitudinal axes 119, 129 enclose a relatively small angle with one another, i.e., they extend approximately parallel to one another. For example, it would be possible for the longitudinal axes 119, 129 to enclose an angle with one another which is less than 20°, optionally less than 10°, further optionally less than 1°. By means of such a parallel configuration of the piezo bender actuators 110, 120, a motion of the piezo bender actuators 110, 120 can be converted particularly efficiently into a motion of the fiber 150. In addition, it is possible that the installation space necessary for the device 100 can be dimensioned to be particularly small. This can apply, for example, with regard to reference implementations in which the piezo bender actuators enclose a relatively large angle with one another.

In the example of FIG. 1, the longitudinal axis 119 is moreover parallel to the longitudinal axis of the fiber 150. In addition, the longitudinal axis 129 is parallel to the longitudinal axis of the fiber 150. In general, it is possible for the longitudinal axes 119, 129 to enclose a relatively small angle with the longitudinal axis of the fiber 150, i.e., they extend approximately parallel to the longitudinal axis of the fiber 150. For example, it would be possible for the longitudinal axis 119 and/or the longitudinal axis 129 to enclose an angle with the longitudinal axis of the fiber 150, which is less than 20°, optionally less than 10°, further optionally less than 1°. Such a parallel arrangement of the piezo bender actuators 110, 120 with respect to the fiber 150 enables a high integration of the device 100. The installation space can be dimensioned to be particularly small. This applies in particular with regard to reference implementations in which an actuator is oriented perpendicularly to the fiber 150 for this purpose.

In the example of FIG. 1, a configuration is shown in which the piezo bender actuators 110, 120 extend along the longitudinal axis 119, 129 thereof away from the movable end 155 of the fiber 150. This means that the region of the deflection of the fiber 150 is arranged away from the piezo bender actuators 110, 120. However, other configurations are also conceivable.

Figure 3:
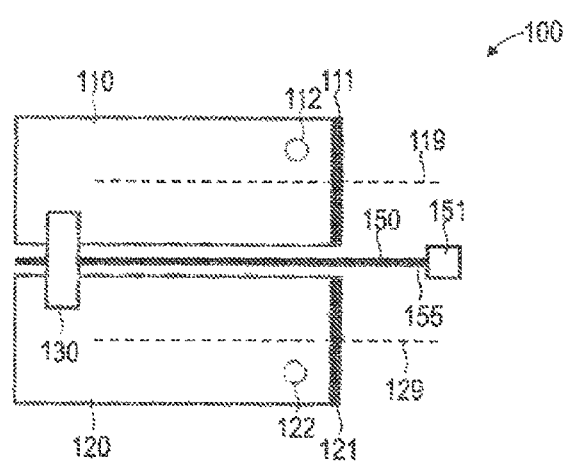
FIG. 3 diagrammatically illustrates a device for the excitation of a fiber, which comprises two piezo bender actuators according to different embodiments.

FIG. 3 illustrates aspects with regard to a device 100. In particular, FIG. 3 illustrates aspects with regard to an arrangement of piezo bender actuators 110, 120 with respect to a fiber 150. The example of FIG. 3 basically corresponds to the example of FIG. 1. However, in the example of FIG. 3, the piezo bender actuators 110, 120 extend along the longitudinal axes 119, 129 thereof toward the movable end 155 of the fiber 150. Thereby, a particularly high integration of the device 100 can be achieved.

For example, from a comparison of FIG. 1 and two it can be seen that, in the example of FIG. 1, the connection part 130 is located between the fastening sites 111, 121 and the movable end 155 of the fiber 150. However, in the example of FIG. 3, the fastening sites 111, 121 are arranged between the connection part 130 and the movable end 155.

Figure 4:
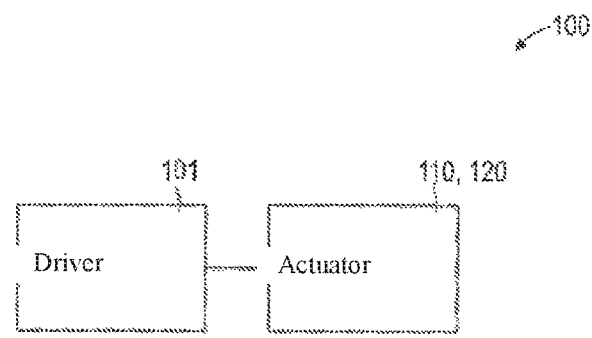
FIG. 4 diagrammatically illustrates a device according to different embodiments, which comprises a driver for at least one actuator, and at least one actuator such as, for example, a piezo bender actuator.

FIG. 4 illustrates aspects with regard to the device 100. In particular, FIG. 4 illustrates aspects with regard to a driver 101 of the motion. For example, the driver 101 could comprise one or more driver circuits. For example, the driver 101 could be configured to output a driver signal with a certain signal form to one or more actuators—for example, the piezo bender actuators 110, 120 and/or magnetic actuators. The driver 101 can have analog components and/or digital components. For example, the driver 101 could be configured to control the actuators as a function of a digital control signal. The driver signal can have certain signal forms which are used for controlling the different actuators. The driver signal is typically an analog signal.

Figure 5:
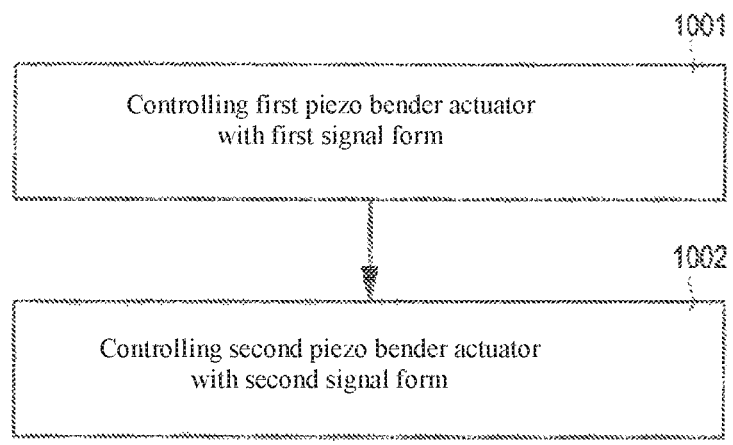
FIG. 5 is a flow chart of a method according to different embodiments.

FIG. 5 is a flow chart of a method according to various examples. For example, the method according to FIG. 5 could be implemented by the driver 101.

First, in block 1001, the first piezo bender actuator 110 is controlled with a first signal form. This can include, for example, providing a voltage and/or a current flow.

Then, in block 1002, the second piezo bender actuator 120 is controlled with a second signal form. This can include, for example, providing a voltage and/or a current flow.

In general, it is possible for the different actuators such as, for example, the piezo bender actuators 110, 120, to be controlled at least partially in a time-parallel manner. In particular, it would be possible for the different actuator phases to be controlled with phase coherence. This can mean that the different signal forms for controlling the different actuators have a well-defined phase relationship.

Figure 6:
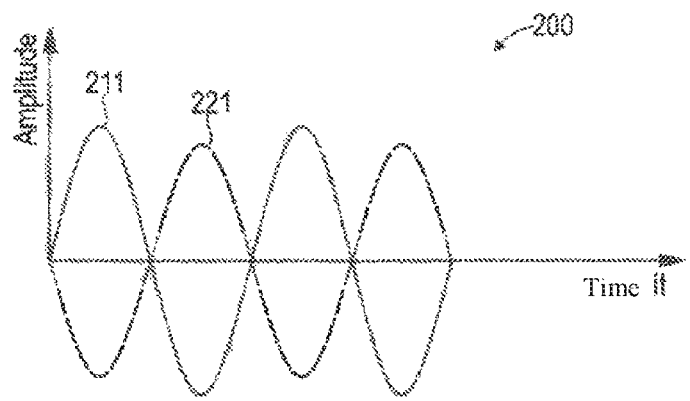
FIG. 6 diagrammatically illustrates signal contributions of signal forms by means of which a driver controls piezo bender actuators according to different embodiments, wherein the signal contributions are configured out-of-phase.

FIG. 6 illustrates aspects with regard to signal forms 200 which can be used to control the piezo bender actuators 110, 120 according to different examples described here. FIG. 6 plots in particular the amplitude of the signal forms 200 as a function of time.

In the example of FIG. 6, a signal contribution 211 (solid line) is represented, which is used to control the piezo bender actuator 110. In addition, in the example of FIG. 6, a signal contribution 221 (dashed line) is represented, which is used to control the piezo bender actuator 120. From the example of FIG. 6, it can be seen that the signal contributions 211, 221 are configured to be out-of-phase. This means, in the example of FIG. 6, that the signal contributions 211, 221 have the same frequency and a phase shift of 180°.

Thereby, it can be achieved that the piezo bender actuator 110 curves or moves upward (curves or moves downward), while the piezo bender actuator 120 curves or moves downward (curves or moves upward). Thereby, in turn, it can be achieved that the connection part 130 is tilted alternatingly to the left and to the right (with respect to the longitudinal axis of the fiber 150). Therefore, with such a configuration of the signal forms 200, in particular an efficient excitation of the torsion mode of the fiber 150 can be achieved.

Figure 7:
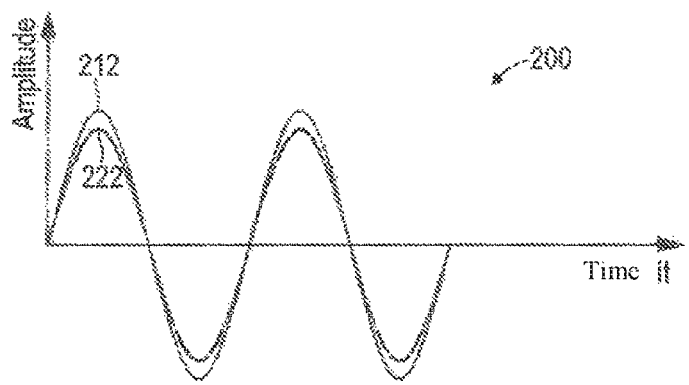
FIG. 7 diagrammatically illustrates signal contributions of signal forms by means of which a driver controls piezo bender actuators according to different embodiments, wherein the signal contributions are configured in-phase.

FIG. 7 illustrates aspects with regard to signal forms 200, which can be used to control the piezo bender actuators 110, 120 according to different examples described herein. FIG. 7 plots in particular the amplitude of the signal forms 200 as a function of time.

In the example of FIG. 7, a signal contribution 212 (solid line) is represented, which is used to control the piezo bender actuator 110. In addition, in the example of FIG. 7, a signal contribution 222 (dashed line) is represented, which is used to control the piezo bender actuator 120. From the example of FIG. 7, one can see that the signal contributions 212, 222 are configured to be in-phase. In the example of FIG. 7, this means that the signal contributions 212, 222 have the same frequency and a phase shift of 0°. In some examples, it would be possible for the in-phase signal contributions 212, 222 to have an amplitude modulation.

By means of the in-phase signal contributions 212, 222, it can be achieved that the piezo bender actuator 110 curves or moves upward (curves or moves downward) while the piezo bender actuator 120 curves or moves upward (curves or moves downward). Thereby, it can be achieved in turn that the connection part 130 is moved alternatingly upward and downward (with respect to the longitudinal axis of the fiber 150). Therefore, with such a configuration of the signal forms 200, a particularly efficient excitation of the transverse mode in the fiber 150 can be achieved.

A typical frequency of the signal contributions 211, 212, 221, 222 in the different examples described herein is, for example, in the range of 50 Hz-1.5 kHz, optionally in the range of 200 Hz-1 kHz, further optionally in the range of 500 Hz-700 Hz. In this way, appropriate image refresh rates can be achieved.

In the examples of FIGS. 6 and 7, scenarios are illustrated, in which, for the excitation of the piezo bender actuators 110, 120, the out-of-phase signal contributions 211, 221 have approximately the same frequency as the in-phase signal contributions 212, 222 for the excitation of the piezo bender actuators 110, 120. In general, it would be possible for the out-of-phase signal contributions 211, 221 to have a first frequency in the range of 95-105% of a second frequency of the in-phase signal contributions 212, 222. By means of such an implementation of the frequencies of the signal forms 200, it can be achieved that a particularly efficient superposition figure of the different degrees of freedom of the motion of the fiber 150—for example, the torsion mode with the transverse mode—can be achieved. In particular, it can be achieved thereby that a high image refresh rate can be achieved, without certain regions of a scanning range being scanned multiple times through nodes in the superposition figure. In particular, such implementations of the frequencies of the signal forms 200 can use the fact that a degeneration of the different excited degrees of freedom of the motion of the fiber 150 is present in the frequency space. For example, it can be possible to achieve a degeneration of the frequency of the torsion mode of the fiber 150 and of the frequency of the transverse mode of the fiber 150 by appropriate configuration of one or more of the following parameters: length of the fiber 150; moment of inertia of the fiber 150 and/or of a balancing weight which is mounted on the fiber 150; and moment of inertia of the optical element 151.

However, in other examples, it would also be possible for the out-of-phase signal contributions 211, 221 to have a first frequency other than the second frequency of the in-phase signal contributions 212, 222. For example, the first frequency of the out-of-phase signal contributions 211, 221 could be in the range of 45-55% of the second frequency of the in-phase signal contributions 212, 222, i.e., approximately half of the second frequency. In other examples, the first frequency could also be approximately double the second frequency or assume an entirely different value. By such an elimination of the degeneration between the different degrees of freedom of the motion of the fiber 150 excited by the out-of-phase signal contributions 211, 221 and the in-phase signal contributions 212, 222, nonlinear interactions between the corresponding degrees of freedom of the motion can be avoided. For example, the formation of a parametric oscillator by the transverse mode and/or the torsion mode can be avoided. Thereby, a particularly targeted excitation of the fiber 150 can be achieved.

From a superposition of the in-phase signal contributions 211, 221 with the out-of-phase signal contributions 212, 222, it can be achieved that the signal form 200 at the piezo bender actuator 110 has a certain phase shift with respect to the signal form 200 at the piezo bender actuator 120. This phase shift can be varied, for example, as a function of the relative amplitude of the in-phase signal contributions 211, 221 and out-of-phase signal contributions 212, 222 with respect to one another. In other words, the actual signal forms 200 can be decomposed into the in-phase signal contributions 211, 221 and the out-of-phase signal contributions 212, 222. In some examples, a function generator used for the generation of the signal forms 200 can already generate the superposition of the in-phase signal contributions 211, 221 with the out-of-phase signal contributions 212, 222.

In some examples described herein, it can be desirable to achieve a large amplitude of the twisting of the deflecting unit 151 by the torsion mode, in order to scan light. For example, the amplitude of the twisting of the deflecting unit 151 can be regulated to a certain target value which is greater than zero and lies in the range of 10°-120°, for example. On the other hand, by a targeted use of the in-phase signal contributions 211, 221, the undesired excitation of the transverse mode by an external shock can be actively damped. For this purpose, for example, a position sensor could be present, which measures the transverse deflection of the deflecting unit 151; then, based on the measurement signal of the position sensor, the amplitude and/or the phase of the in-phase signal contributions 211, 221 can be adjusted; for example, a control loop could be implemented, which specifies a minimum transverse deflection of the deflecting unit 151 as target variable. Alternatively or additionally to the measuring of the transverse deflection of the deflecting unit 151, an acceleration sensor could be arranged in the reference coordinate system of the unmoved ends 111, 121 and measure the external shock.

Figure 8:
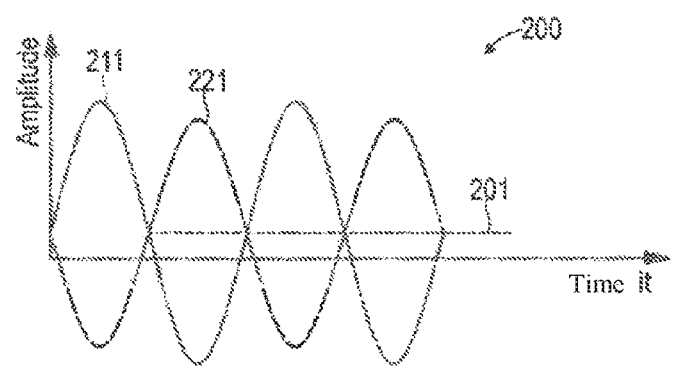
FIG. 8 diagrammatically illustrates signal contributions of signal forms by means of which a driver controls piezo bender actuators according to different embodiments, wherein the signal contributions are configured out-of-phase and have a DC portion.

FIG. 8 illustrates aspects with regard to signal forms 200, which can be used in order to control the piezo bender actuators 110, 120 according to different examples described herein. FIG. 8 in particular plots the amplitude of the signal forms 200 as a function of time.

The example of FIG. 8 basically corresponds to the example of FIG. 6; however, in the example of FIG. 8, the signal contributions 211, 221 in each case have a DC portion 201. In some examples, it would also be possible for only one of the signal contributions 211, 221 to have a DC portion 201 (horizontal dashed line in FIG. 8). In some examples, it would also be possible for the two signal contributions 211, 221 to have differently dimensioned DC portions 201, differing, for example, in magnitude and/or sign.

By the provision of the DC portion 201, it can be achieved that a bias of the fiber 150, i.e., a DC deflection of the fiber 150, is implemented. Thereby, for example, an offset of the fiber and/or specifications for the field of view of the corresponding scanner can be compensated or taken into consideration.

Figure 9:
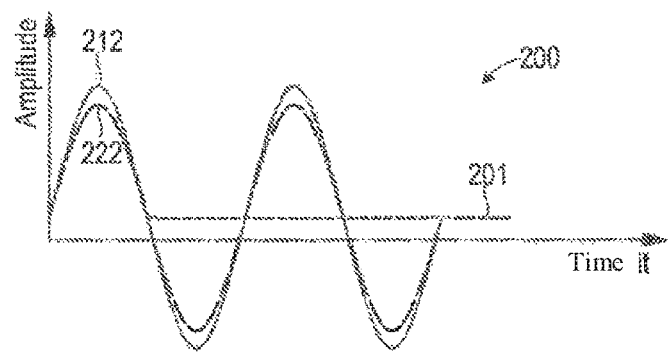
FIG. 9 diagrammatically illustrates signal contributions of signal forms by means of which a driver controls piezo bender actuators according to different embodiments, wherein the signal contributions are configured in-phase and have a DC portion.

FIG. 9 illustrates aspects with regard to signal forms 200 which can be used in order to control the piezo bender actuators 110, 120 according to different examples described herein. FIG. 9 in particular plots the amplitude of the signal forms 200 as a function of time.

The example of FIG. 9 basically corresponds to the example of FIG. 7. However, in the example of FIG. 9, the signal contributions 212, 222 have a respective DC portion 201. In general, it is possible that only some of the signal contributions 211, 212, 221, 222 have the DC portion 201. It would also be possible for different signal contributions 211, 212, 221, 222 to have differently dimensioned DC portions 201.

Figure 10:
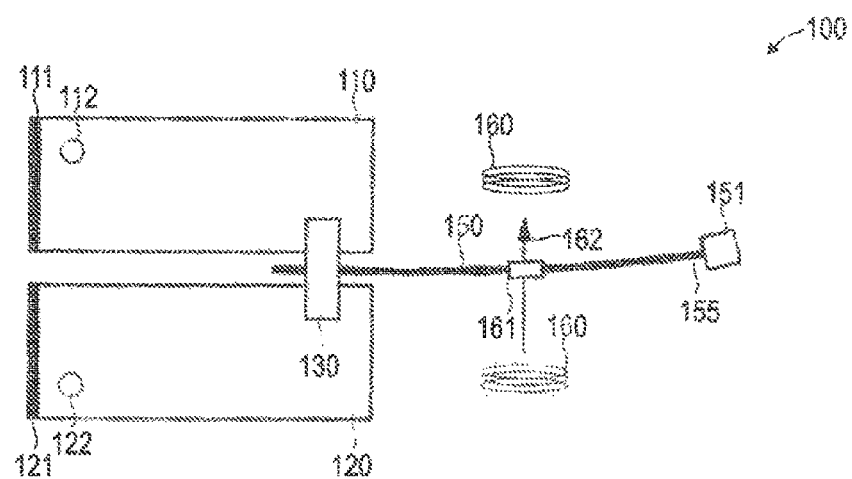
FIG. 10 diagrammatically illustrates a device for the excitation of a fiber, which comprises two piezo bender actuators and a magnetic field source according to different embodiments.

FIG. 10 illustrates aspects with regard to a device 100. The example of FIG. 10 basically corresponds to the example of FIG. 1. In the example of FIG. 10, the device 100 further comprises a magnet 161 which is mounted on the fiber 150. In particular, the magnet 161 is mounted on the fiber 150 in a region which is arranged between the movable end 155 and the connection part 130. For example, the magnet 161 could be a ferromagnetic bulk material. For example, the magnet 161 could form a balancing weight. For example, the magnet 161 could be designed as a thin-film coating of a surface of the fiber 150, for example, with a layer thickness in the range of 20-500 nm. In the example of FIG. 10, the device 100 also comprises a magnetic field source 160. For example, the magnetic field source 160 could be implemented by coil windings which, for example, have an iron yoke (not represented in FIG. 10). By means of the magnetic field source 160—which can be controlled, for example, by the driver 101—, it can be possible to apply a bias to the fiber 150. For this purpose, the driver 101 can control the magnetic field source 160 with a signal form which has a DC portion and thus implements a DC magnetic field 162. In the example of FIG. 10, a DC deflection of the fiber 150 due to the magnetic field 162 which is generated by the magnetic field source 160 is represented. This bias of the fiber 150 brings about a curving of the fiber 150, whereby, for example, light is radiated by means of the deflecting unit 151 in a resting state of the fiber 150 at a radiation angle different from without curving. Thereby, for example, an offset of the fiber, for example, due to drift and/or specifications for the field of view of the corresponding scanner, can be compensated or taken into consideration. This DC deflection of the fiber 150 can then be superposed with AC deflections which, for example, can be applied by the signal forms 200 which are used by the piezo bender actuators 110, 120.

Figure 11:
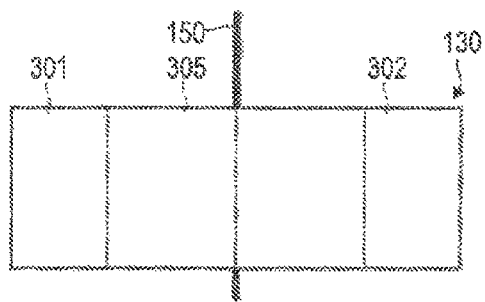
FIG. 11 is a diagrammatic view onto a connection part which according to different embodiments is arranged between two piezo bender actuators.

FIG. 11 illustrates aspects with regard to the connection part 130. FIG. 11 is a view onto the connection part 130. The connection part 130 has a side region 301 and a side region 302 opposite the side region 301. In between, a central region 305 is arranged. In the central region 305, an indentation 306 can be arranged which can be obtained by a curving of the central region 305 with respect to the side regions 301, 302 (oriented out of the plane of the drawing of FIG. 11 or into the plane of the drawing of FIG. 11). The side regions 301, 302 can form contact surfaces on which the piezo bender actuators 110, 120 are mounted, for example, by adhesive.

Figure 12:
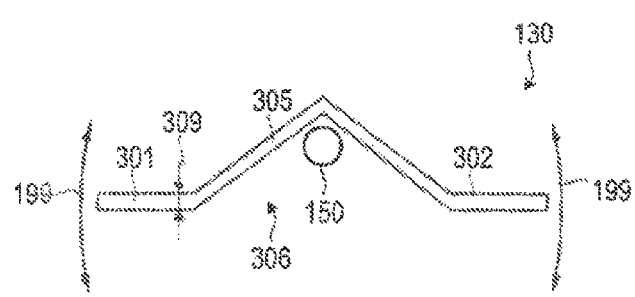
FIG. 12 is a diagrammatic side view of the connection part according to FIG. 11.

FIG. 12 illustrates aspects with regard to the connection part 130. FIG. 12 is a view onto the connection part 130 according to the example of FIG. 11. In FIG. 12, it can be seen that the fiber 150 is arranged in the region of the indentation 306 on the connection part 130. For example, the fiber 150 can be glued on the connection part 130 in the region of the indentation 306.

By the formation of the indentation 306, a particularly firm coupling between the connection part 130 and the fiber 150 can be achieved. For example, the indentation 300 can be designed to be U-shaped. In the area of the "bottom" of the U-shaped region formed in this manner, a guide for the fiber 150 along the longitudinal axis of the fiber 150 can then be provided. This can ensure a particularly large flux of force by deflection 199 of the piezo bender actuators 110, 120, without rupturing occurring.

Figure 13:
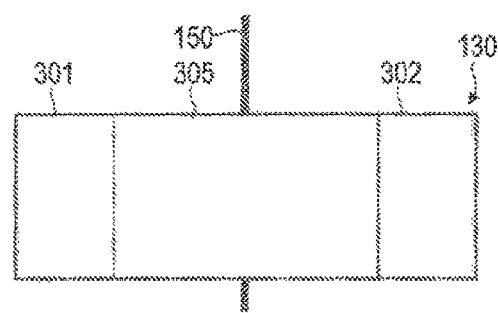
FIG. 13 is a diagrammatic view onto a connection part which according to different embodiments is arranged between two piezo bender actuators.
Figure 14:
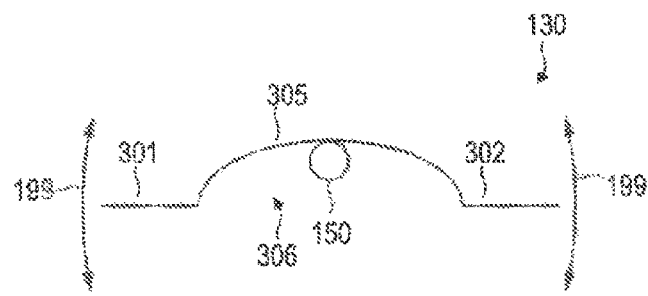
FIG. 14 is a diagrammatic side view of the connection part according to FIG. 13.

FIGS. 13 and 14 illustrate aspects with regard to the connection part 130. Here, FIG. 13 is a view onto the connection part 130, and FIG. 14 is a side view of the connection part 230. The example of FIGS. 13 and 14 basically corresponds to the example of FIGS. 11 and 12. In the example of FIGS. 13 and 14, the connection part 130 is also designed to be U-shaped. However, the indentation 306 does not taper to a point but instead has a continuous curvature. Thereby, the material stability of the connection part 130 can be increased. In addition, a steep pitch can be prevented.

Such a continuous transition could be implemented between the side regions 301, 302 and the central region 305 (not represented in FIG. 14).

In the various examples described herein, it would be possible for the connection part 130 to be made of metal. For example, the connection part 130 could be made of steel. It would also be possible for the connection part 130 to be made of brass. In this manner, a sufficiently high stability for the connection part 130 can be provided, so that, due to the deflection 199 of the piezo bender actuators 110, 120, no or no significant material fatigue of the connection part 130 occurs.

However, in other examples, the connection part 130 could also be made of the same material as the fiber 150. For example, the connection part 130 and the fiber 150 could be designed to form a single piece made of the same material. For this purpose, for example, a micro-machining attachment can be used, in which the fiber 150 and the connection part 130 are released from a wafer—for example, a silicon wafer or a silicon on isolator wafer. In this manner, a particularly robust coupling between fiber 150 and connection part 130 can be brought about. In particular, in such scenarios, it can be possible for the connection part 130 to have no indentation and to be designed instead to be flat. The connection part 130 can extend in the same plane as the fiber 150.

In some examples, it can be desirable if the connection part has a particularly small thickness 309. For example, the thickness 309 of the connection part 230 could be in the range of 5-150 µm, optionally in the range of 10-100 µm, further optionally in the range of 40-60 µm. In this manner, it can be achieved that the connection part 130 has a certain resilience and as a result it does not or does not significantly damp the deflection 199 of the piezo bender actuators 110, 120. Thereby, the fiber 150 can be excited with a large amplitude.

Figure 15:
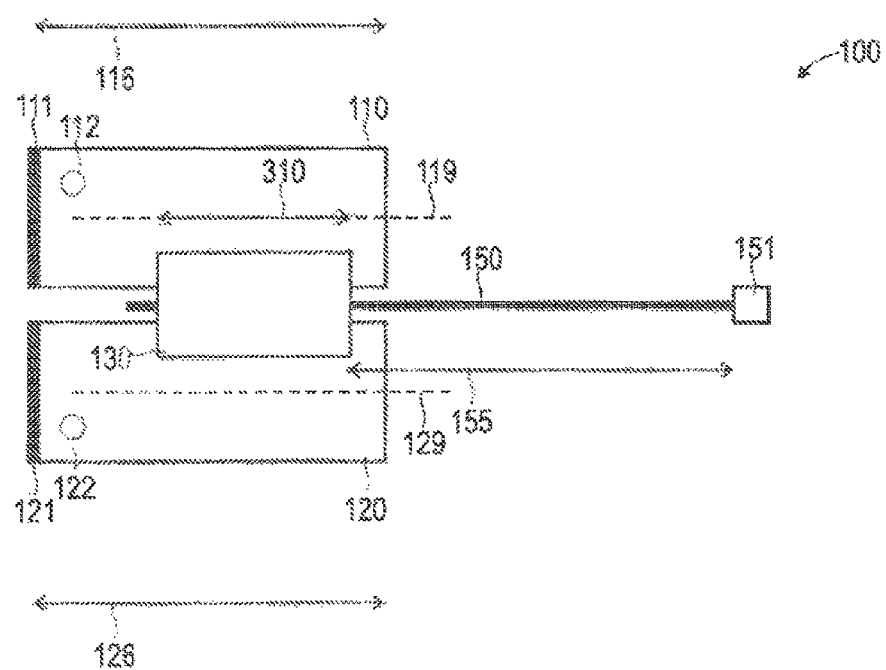
FIG. 15 diagrammatically illustrates a device for the excitation of a fiber, which comprises two piezo bender actuators according to different embodiments.

FIG. 15 illustrates aspects with regard to the device 100. In particular, FIG. 15 illustrates aspects with regard to a dimensioning of the connection part 130 with respect to the piezo bender actuators 110, 120 or the fiber 150. The example of FIG. 15 basically corresponds to the example of FIG. 1, but in the example of FIG. 15, the connection part 130 is dimensioned to be longer than in the example of FIG. 15. This means that the longitudinal extension 310 of the connection part 130 parallel to the longitudinal axes 119, 129 of the piezo bender actuators 110, 120 is dimensioned to be larger in the example of FIG. 15 than in the example of FIG. 1.

For example, in general, it would be possible for the connection part 130 to have a longitudinal extension 310 along the longitudinal axes 110, 129 of the piezo bender actuators 110, 120 which is in the range of 2-20% of the lengths 116, 126 of the piezo bender actuators 110, 120, optionally in the range of 5-15%. By such a dimensioning of the longitudinal extension 310 of the connection part 130, it is possible, on the one hand, to ensure that the deflection 199 of the piezo bender actuators 110, 120 is not damped particularly strongly by the connection part 130. Thereby, the motion of the fiber 150 can be excited with a large amplitude. On the other hand, it can be ensured that the flux of force between the piezo bender actuators 110, 120 via the connection part 130 and onto the fiber 150 does not bring about excessively large biases in a small spatial region. Thereby, the device 100 can be implemented to be more stable.

In summary, techniques which enable a particularly efficient excitation of a fiber have been described above. The above-described techniques enable in particular an efficient excitation of the fiber with a relatively high integration of the corresponding device. This means that different degrees of freedom of motion of the fiber can be excited without the corresponding device having a large space requirement.

In the different techniques described herein, it can be possible in particular that a device used for the excitation of the fiber has an elongate design. This can be due to the fact that the fiber has a longitudinal axis which extends substantially parallel to the longitudinal axes of two or more piezo bender actuators. For example, in absolute dimensions, the fiber can have an extension in the range of 2-10 mm along the longitudinal axis thereof. Accordingly, it would be possible, for example, for the piezo bender actuators used to have an extension along the longitudinal axes thereof in the range of 2-20 mm.

Based on such techniques, a particularly flexible integration of a corresponding device in a system can occur. For example, a corresponding device for a LIDAR system could be integrated in a motor vehicle.

Figure 16:
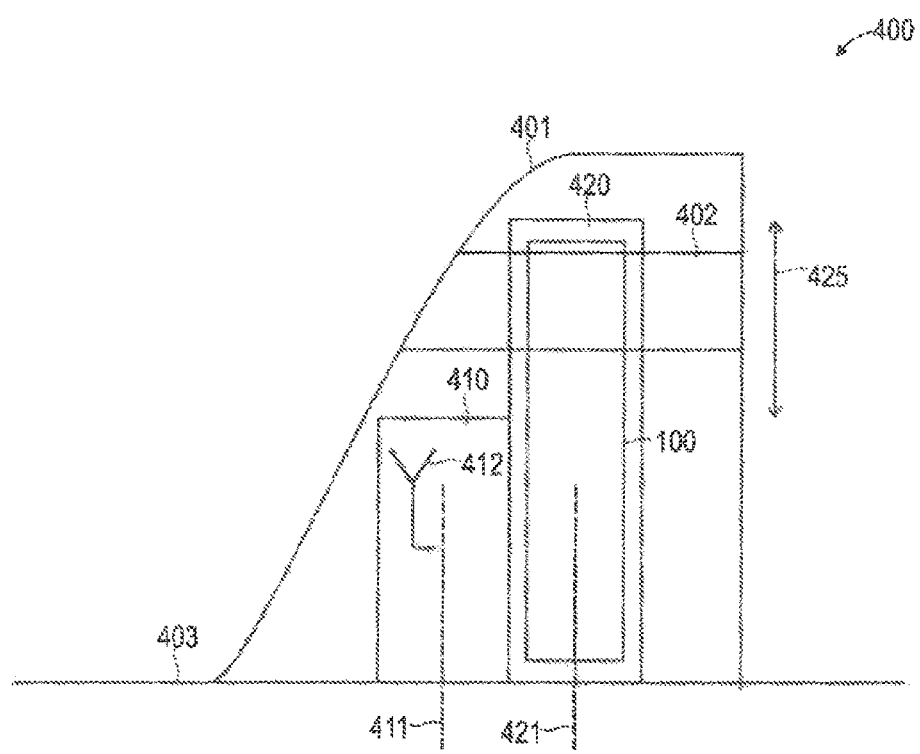
FIG. 16 diagrammatically illustrates a system according to different embodiments, which comprises a first housing with a high-frequency antenna and a second housing with a device for the excitation of a fiber according to various examples.

FIG. 16 illustrates aspects with regard to a system 400. In particular, FIG. 16 illustrates aspects with regard to the integration of the device 100 in the system 400.

The system 400 comprises an elongate housing 410 and an additional elongate housing 420. The elongate housings 410, 420 are arranged parallel to one another. Therefore, the housing 420 extends along the housing 410. The system 400 also comprises a high-frequency antenna 412 which is arranged in the housing 410. For example, the high-frequency antenna 412 could be used for radio reception, television reception, satellite reception and/or mobile radio reception, etc.

The device 100 according to different examples described herein is arranged in the housing 420. Both the housing 420 and the housing 410 are integrated in an additional housing 401 of the system 400. For example, the housing 401 could be have a shark-fin form and be arranged, for example, in the region of a roof of a motor vehicle. The housing 401 and the housing 420 comprise a transparent window 402. The transparent window 402 can in particular be translucent to light deflected by the deflecting unit 151 of the fiber 150. For example, the deflection unit 151 could be in the region of the window 402.

In the example of FIG. 16, longitudinal axes 411, 421 of the housings 410, 420 are also represented. For example, it would be possible for the longitudinal axis 421 of the housing 420 to extend parallel to the longitudinal axis of the fiber 150 or parallel to the longitudinal axis 119 of the piezo bender actuator 110 and/or parallel to the longitudinal axis 129 of the piezo bender actuator 120. Thereby, a particularly small extension of the housing 420 perpendicularly to the longitudinal axis 421 and thus a high integration can be achieved.

From the example of FIG. 16, it can be seen that the housing 420 extends in an exposed region 425 beyond the housing 410. Thereby, it can be achieved that the window 402 arranged in the exposed region 425 has, perpendicular to the longitudinal axis 421, a large extension of, for example, no less than 50°, optionally no less than 120°, further optionally no less than 200°, further optionally of 360°. This can mean that the light can be radiated in a large surrounding region by means of the deflecting unit 151. For LIDAR techniques, this can have the advantage of larger fields of view. At the same time, the deflection of the light is not blocked by the housing 410.

The housings 410, 420 have a common base plate 403. The base plate 403 is arranged opposite the exposed region 425. For example, it would be possible for the base plate 403 to be mounted on a surface of a roof of a motor vehicle. By means of such a mounting of the device 100 in a high position, a particularly large far vision can be achieved in LIDAR systems implemented by means of the device 100.

Naturally, the features of the above-described embodiments and aspects of the invention can be combined with one another. In particular, the features can be used not only in the described combinations but also in other combinations or alone, without leaving the field of the invention.

For example, various examples have been described above with regard to laser light. However, corresponding techniques can also be used for other light.

Furthermore, various examples have been described above with regard to laser light, wherein a connection part with an indentation is used. However, in other examples, it would also be possible for the connection part to be designed flat and without indentation.

The invention claimed is:

1. A device for the excitation of a fiber-shaped element, which comprises:
   a first piezo bender actuator,
   a second piezo bender actuator,
   a connection part, which is arranged between the first piezo bender actuator and the second piezo bender actuator, and
   a movable fiber-shaped element, which is mounted to the connection part;
   wherein the first and second piezo bender actuators each are planar, in a resting position, and wherein the first and second piezo bender actuators are co-planar in a direction that is perpendicular to a direction of a bending of the first and second piezo bender actuators.

2. The device according to claim 1,
   wherein the first piezo bender actuator has an elongate form along a first longitudinal axis,
   wherein the second piezo bender actuator has an elongate form along a second longitudinal axis,
   wherein the first longitudinal axis and the second longitudinal axis enclose an angle with one another which is less than 20°.

3. The device according to claim 1,
   wherein the first piezo bender actuator has an elongate form along a first longitudinal axis,
   wherein the second piezo bender actuator has an elongate form along a second longitudinal axis,
   wherein the first longitudinal axis and/or the second longitudinal axis enclose an angle with a longitudinal axis of the fiber-shaped element which is less than 20°.

4. The device according to claim 1,
   wherein the connection part has an indentation,
   wherein the fiber-shaped element is mounted in a region of the indentation.

5. The device according to claim 1,
   wherein the connection part is made of metal and has a thickness in the range of 5-150 µm.

6. The device according to claim 1,
   wherein the connection part has a longitudinal extension along a first longitudinal axis of the first piezo bender actuator which is in the range of 2-20% of the length of the first piezo bender actuator along the first longitudinal axis, and/or
   wherein the connection part has a longitudinal extension along a second longitudinal axis of the second piezo bender actuator, which is in the range of 2-20% of the length of the second piezo bender actuator along the second longitudinal axis, optionally in the range of 5-15%.

7. The device according to claim 1,
   wherein the first piezo bender actuator has an elongate form along a first longitudinal axis,
   wherein the second piezo bender actuator has an elongate form along a second longitudinal axis,
   wherein the first piezo bender actuator extends along the first longitudinal axis and the second piezo bender actuator extends along the second longitudinal axis along a longitudinal axis of the fiber-shaped element toward a freely movable end of the fiber-shaped element.

8. The device according to claim 1, which further comprises:
   a driver, which is configured to control the first piezo bender actuator with a first signal form and to control the second piezo bender actuator with a second signal form,
   wherein the first signal form and the second signal form have out-of-phase signal contributions.

9. The device according to claim 8,
   wherein the fiber-shaped element is mounted to a first end on the connection part
   wherein an optical element of the device is mounted to a second end of the fiber-shaped element which is opposite the first end,
   wherein the driver is configured to bring about a twisting of the optical element by means of the out-of-phase signal contributions for scanning light by means of the optical element.

10. The device according to claim 8,
    wherein the first signal form and the second signal form have additional in-phase signal contributions which are optionally amplitude modulated.

11. The device according to claim 10,
wherein the fiber-shaped element is mounted to a first end on the connection part,
wherein an optical element is mounted to a second end of the fiber-shaped element which is opposite the first end,
wherein the driver is configured to damp a transverse deflection of the optical element by means of the in-phase signal contributions.

12. The device according to claim 10, wherein the signal contributions have a first frequency,
wherein the additional in-phase signal contributions have a second frequency,
wherein the first frequency is in the range of 95-105% of the second frequency or in the range of 45-55% of the second frequency.

13. The device according to claim 1, which further comprises:
a driver, which is configured to control the first piezo bender actuator with a first signal form and to control the second piezo bender actuator with a second signal form,
wherein the first signal form has a signal contribution with a frequency of no less than 200 Hz wherein the second signal form has a signal contribution with a frequency of no less than 200 Hz.

14. The device according to claim 13,
wherein the first signal form and/or the second signal form has/have a DC portion.

15. The device according to claim 1, which further comprises:
a magnet, which is mounted to the fiber-shaped element, and
a magnetic field source, which is configured to generate a magnetic field with variable orientation in a region of the magnet.

16. The device according to claim 15, which further comprises:
a driver, which is configured to control the magnetic field source with a signal form which has a DC portion.

17. A method for exciting a fiber-shaped element which extends away from a connection part which is arranged between a first piezo bender actuator and a second piezo bender actuator, wherein the first and second piezo bender actuators each planar, in a resting position, and wherein the first and second piezo bender actuators are co-planar in a direction that is perpendicular to a direction of a bending of the first and second piezo bender actuators, the method comprising:
controlling the first piezo bender actuator with a first signal form, and
controlling the second piezo bender actuator with a second signal form.

18. The method according to claim 17,
wherein the first signal form and the second signal form have out-of-phase signal contributions.

19. The method according to claim 18, which further comprises:
wherein the fiber-shaped element is mounted to a first end on the connection part,
wherein an optical element is mounted to a second end of the fiber-shaped element which is opposite the first end,
wherein the method further comprises:
bringing about a twisting of the optical element by means of the out-of-phase signal contributions for a scanning of light by means of the optical element.

20. The method according to of claim 17,
wherein the first signal form and the second signal form have in-phase signal contributions which are optionally amplitude modulated.

21. The method according to claim 20,
wherein the fiber-shaped element is mounted to a first end on the connection part,
wherein an optical element is mounted to a second end of the fiber-shaped element which is opposite the first end,
wherein the method further comprises:
damping a transverse deflection of the optical element by means of the in-phase signal contributions.

22. A system which comprises:
an elongate first housing,
an elongate second housing which extends at least in a section along the first housing,
a high-frequency antenna which is arranged in the first housing, and
a device arranged in the second housing, the device comprising:
a first piezo bender actuator,
a second piezo bender actuator,
a connection part, which is arranged between the first piezo bender actuator and the second piezo bender actuator, and
a movable fiber-shaped element, which is mounted to the connection part.

23. The system according to claim 22,
wherein the second housing extends in an exposed region beyond the first housing, wherein, in the exposed region, the second housing has a transparent window having, perpendicular to a longitudinal axis of the first housing, an extension of no less than 50°.

24. The system according to claim 23,
wherein the first housing and the second housing have a common base plate which is arranged opposite the exposed region.

* * * * *